(12) United States Patent
Sugiyama et al.

(10) Patent No.: US 10,330,579 B2
(45) Date of Patent: Jun. 25, 2019

(54) PARTICULATE MEASUREMENT SYSTEM

(71) Applicant: NGK SPARK PLUG CO., LTD., Nagoya-shi, Aichi (JP)

(72) Inventors: Takeshi Sugiyama, Ichinomiya (JP); Masayuki Motomura, Komaki (JP); Toshiya Matsuoka, Gifu (JP); Keisuke Tashima, Kasugai (JP)

(73) Assignee: NGK SPARK PLUG CO., LTD., Aichi (JP)

(*) Notice: Subject to any disclaimer, the term of this patent is extended or adjusted under 35 U.S.C. 154(b) by 1182 days.

(21) Appl. No.: 14/515,608

(22) Filed: Oct. 16, 2014

(65) Prior Publication Data

US 2015/0120229 A1 Apr. 30, 2015

(30) Foreign Application Priority Data

Oct. 25, 2013 (JP) ................. 2013-222167

(51) Int. Cl.
| | |
|---|---|
| G01N 15/06 | (2006.01) |
| G01L 3/00 | (2006.01) |
| G01M 15/10 | (2006.01) |
| G01P 3/00 | (2006.01) |
| H01J 49/02 | (2006.01) |
| H01T 23/00 | (2006.01) |
| G01N 15/00 | (2006.01) |

(52) U.S. Cl.
CPC ............ *G01N 15/0656* (2013.01); *G01L 3/00* (2013.01); *G01M 15/102* (2013.01); *G01N 15/0606* (2013.01); *G01P 3/00* (2013.01); *H01J 49/02* (2013.01); *H01T 23/00* (2013.01); *G01N 2015/0046* (2013.01)

(58) Field of Classification Search
CPC ..................................... G01N 15/06
See application file for complete search history.

(56) References Cited

U.S. PATENT DOCUMENTS

| | | | |
|---|---|---|---|
| 8,652,240 B2 | 2/2014 | Sugiyama et al. | |
| 2004/0128985 A1* | 7/2004 | Shimasaki | F01N 3/0253 60/286 |
| 2010/0000404 A1* | 1/2010 | Sakuma | G01N 15/0656 95/3 |
| 2011/0203931 A1* | 8/2011 | Novosselov | G01N 1/2202 204/600 |
| 2012/0186330 A1 | 7/2012 | Ueno et al. | |

(Continued)

FOREIGN PATENT DOCUMENTS

| | | |
|---|---|---|
| JP | 2000-161043 A | 6/2000 |
| JP | 2010-25885 A | 2/2010 |

(Continued)

OTHER PUBLICATIONS

Communication dated Dec. 20, 2017 from the Japanese Patent Office in counterpart application No. 2014-217843.

*Primary Examiner* — Marc Anthony Armand
(74) *Attorney, Agent, or Firm* — Sughrue Mion, PLLC

(57) ABSTRACT

A particulate amount determination section of a particulate measurement system corrects a measurement signal or the amount of particulates determined from the measurement signal based on one or a plurality of three operating condition parameters selected from speed of the vehicle, rotational speed of the internal combustion engine and torque of the internal combustion engine.

5 Claims, 10 Drawing Sheets

(56) References Cited

U.S. PATENT DOCUMENTS

| | | | | |
|---|---|---|---|---|
| 2012/0234172 A1* | 9/2012 | Sugiyama | ............ | G01N 1/2252 |
| | | | | 96/26 |
| 2012/0262182 A1 | 10/2012 | Matsuoka et al. | | |
| 2012/0290177 A1* | 11/2012 | Wagenhuber | ....... | B60R 25/2045 |
| | | | | 701/49 |
| 2014/0172280 A1* | 6/2014 | Ogata | .................... | G01H 17/00 |
| | | | | 701/111 |

FOREIGN PATENT DOCUMENTS

| | | |
|---|---|---|
| JP | 2012-150028 A | 8/2012 |
| JP | 2012-194078 A | 10/2012 |
| JP | 2012-220423 A | 11/2012 |

* cited by examiner

CORRECTION BASED ON ROTATIONAL SPEED

PARTICULATE MEASUREMENT SYSTEM

BACKGROUND OF THE INVENTION

1. Field of the Invention

The present invention relates to a particulate measurement system which measures the amount of particulates such as soot contained in a gas.

2. Description of the Related Art

Conventionally, a particulate measurement system has been known which measures the amount of particulates such as soot contained in exhaust gas discharged from an internal combustion engine such as a diesel engine (Patent Documents 1 and 2). This particulate measurement system generates ions by means of corona discharge, electrifies particulates contained in the exhaust gas by the generated ions, captures ions not used for electrification of particulates, and measures the amount of particulates contained in the exhaust gas based on the amount of trapped ions (in other words, based on the amount of ions used for electrification of particulates that were not trapped). The amount of trapped ions correlates with the amount of ions used for electrification, and the amount of ions used for the electrification correlates with the amount of particulates contained in the exhaust gas. Therefore, the particulate measurement system can measure the amount of particulates contained in the exhaust gas flow from the amount of trapped ions.

[Patent Document 1] Japanese Patent Application Laid-Open (kokai) No. 2012-220423

[Patent Document 2] Japanese Kohyo (PCT) Patent Publication No. 2012-194078

3. Problems to be Solved by the Invention

The present inventors found that the relation between a measurement signal representing a current corresponding to the above-described amount of ions and the amount of particulates changes in accordance with specific operating conditions of an internal combustion engine and a vehicle, such that the resulting measurement accuracy is low.

SUMMARY OF THE INVENTION

It is therefore an object of the present invention to solve the above-described problems, and more particularly, to provide a particulate measurement system which takes into account the specific operating conditions of an internal combustion engine and a vehicle to thereby obtain increased measurement accuracy.

The above object has been achieved by providing (1) a particulate measurement system comprising an ion generation section for generating ions by corona discharge; an electrification chamber for electrifying at least a portion of particulates contained in exhaust gas discharged from an internal combustion engine of a vehicle with said ions; a trapping section for trapping at least a portion of the ions not used for electrification of the particulates; a measurement signal generation circuit for generating a measuring signal correlating with an amount of particulates contained in the exhaust gas, based on a current corresponding to a difference between an amount of ions generated by the ion generation section and an amount of ions trapped in the trapping section; and a particulate amount determination section for determining the amount of particulates contained in the exhaust gas based on the measurement signal, wherein the particulate amount determination section corrects the measurement signal or the amount of particulates determined from the measurement signal based on one or a plurality of three operating condition parameters selected from the group consisting of speed of the vehicle, rotational speed of the internal combustion engine and torque of the internal combustion engine.

According to the particulate measurement system (1), the measurement signal or the amount of particulates is corrected based on one or a plurality of the above-mentioned three operating condition parameters. Therefore, it is possible to suppress loss of measurement accuracy which occurs due to the relation between the measurement signal and the amount of particulates which changes in accordance with operating conditions of the vehicle.

In a preferred embodiment (2) of the particulate measurement system (1) above, the correction is performed based on all of the three operating condition parameters.

According to this configuration, the effect of suppressing the loss of measurement accuracy is higher as compared with the case where the correction is performed based on one or two of the three operating condition parameters.

In another preferred embodiment (3) of the particulate measurement system (1) or (2) above, the correction is performed in accordance with the following equation:

$$y = y_0 \times \alpha(Vh) \times \beta(Neg) \times \gamma(Teg)$$

wherein y is the measurement signal or the amount of particulates after correction, $y_0$ is the measurement signal or the amount of particulates before correction, Vh is the speed of the vehicle, Neg is the rotational speed of the internal combustion engine, Teg is the torque of the internal combustion engine, and $\alpha(Vh)$, $\beta(Neg)$, and $\gamma(Teg)$ are coefficients determined in accordance with corresponding parameters Vh, Neg and Teg.

According to this configuration, the loss in measurement accuracy is suppressed by performing the correction in accordance with the above-described equation.

In yet another preferred embodiment (4) of the particulate measurement system (3) above, each of the coefficients $\alpha(Vh)$, $\beta(Neg)$, and $\gamma(Teg)$ is a step function which provides a fixed coefficient value for each of a plurality of ranges of the corresponding parameter.

According to this configuration, it is possible to perform proper correction using simple equations employing the three operating condition parameters Vh, Neg and Teg.

In yet another preferred embodiment (5) of the particulate measurement system (1) or (2) above, the correction is performed in accordance with the following equation:

$$y = y_0 \times \delta(Vh, Neg, Teg)$$

wherein y is the measurement signal value or the amount of particulates after correction, $y_0$ is the measurement signal value or the amount of particulates before correction, Vh is the speed of the vehicle speed, Neg is the rotational speed of the internal combustion engine, Teg is the torque of the internal combustion engine, and $\delta(Vh, Neg, Teg)$ is a coefficient determined in accordance with the corresponding parameters Vh, Neg and Teg.

According to this configuration, the loss of measurement accuracy is suppressed by performing the correction in accordance with the above-described equation.

Notably, the present invention can be realized in various forms. For example, the present invention can be realized as a particulate sensor, a particulate detection method, an internal combustion engine including a particulate measurement system, or a vehicle including the internal combustion engine.

DESCRIPTION OF REFERENCE NUMERALS AND SYMBOLS

Figure 1A:
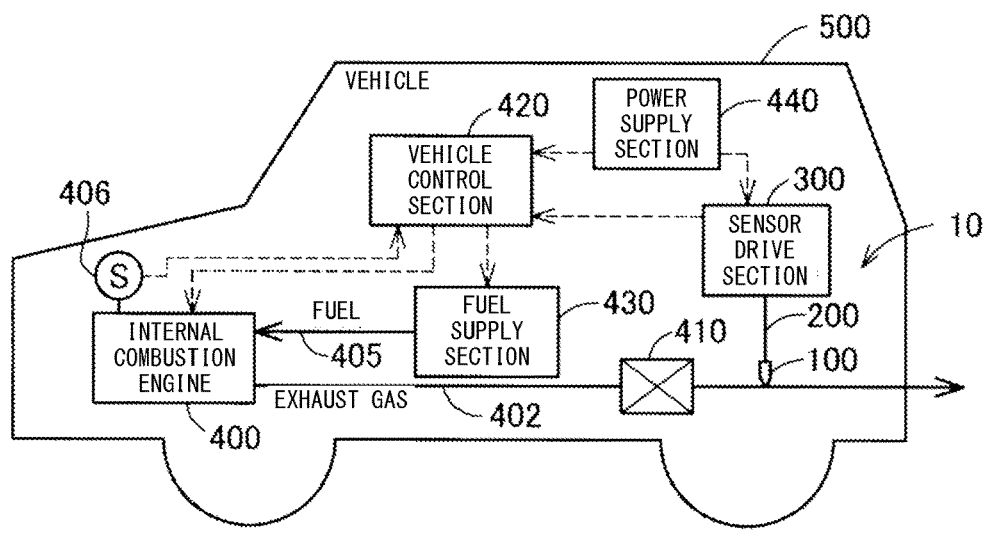
FIGS. 1(a) and 1(b) are explanatory views showing the configuration of a particulate measurement system according to one embodiment.

Reference numerals and symbols used to identify various features in the drawings include the following.

10 . . . particulate measurement system
25 . . . ceramic pipe
31 . . . gas flow passage
35 . . . discharge hole
41 . . . nozzle
42 . . . partition wall
45 . . . inflow hole
55 . . . air supply hole
100 . . . particulate sensor
110 . . . ion generation section
111 . . . ion generation chamber
112 . . . first electrode
120 . . . exhaust gas electrification section
121 . . . electrification chamber
130 . . . ion trapping section
131 . . . trapping chamber
132 . . . second electrode
200 . . . cable
221 . . . first wiring line
222 . . . second wiring line
223 . . . signal line
224 . . . air supply tube
230 . . . shunt resistor
300 . . . sensor drive section
400 . . . internal combustion engine
402 . . . exhaust gas pipe
405 . . . fuel pipe
410 . . . filter apparatus
420 . . . vehicle control section
430 . . . fuel supply section
440 . . . power supply section
500 . . . vehicle
600 . . . sensor control section
700 . . . electric circuit section
710 . . . primary-side power supply circuit
711 . . . discharge voltage control circuit
712 . . . transformer drive circuit
720 . . . isolation transformer
730 . . . corona current measurement circuit
740 . . . measurement signal generation circuit
745 . . . offset voltage adjustment circuit
751, 752 . . . rectification circuit
753, 754 . . . resistor for short protection
771-774 . . . wiring line
800 . . . air supply section
AMP1-AMP2 . . . amplification circuit (operational amplifier)
CS . . . casing
PGL . . . primary-side ground
R1-R4 . . . resistor
SW . . . switch
SGL . . . secondary-side ground
$V_{ref}$ . . . reference voltage
$V_{offset}$ . . . offset voltage

DETAILED DESCRIPTION OF THE PREFERRED EMBODIMENTS

The invention is next described in greater detail with reference to the drawings. However, the present invention should not be construed as being limited thereto.

Figure 1B:
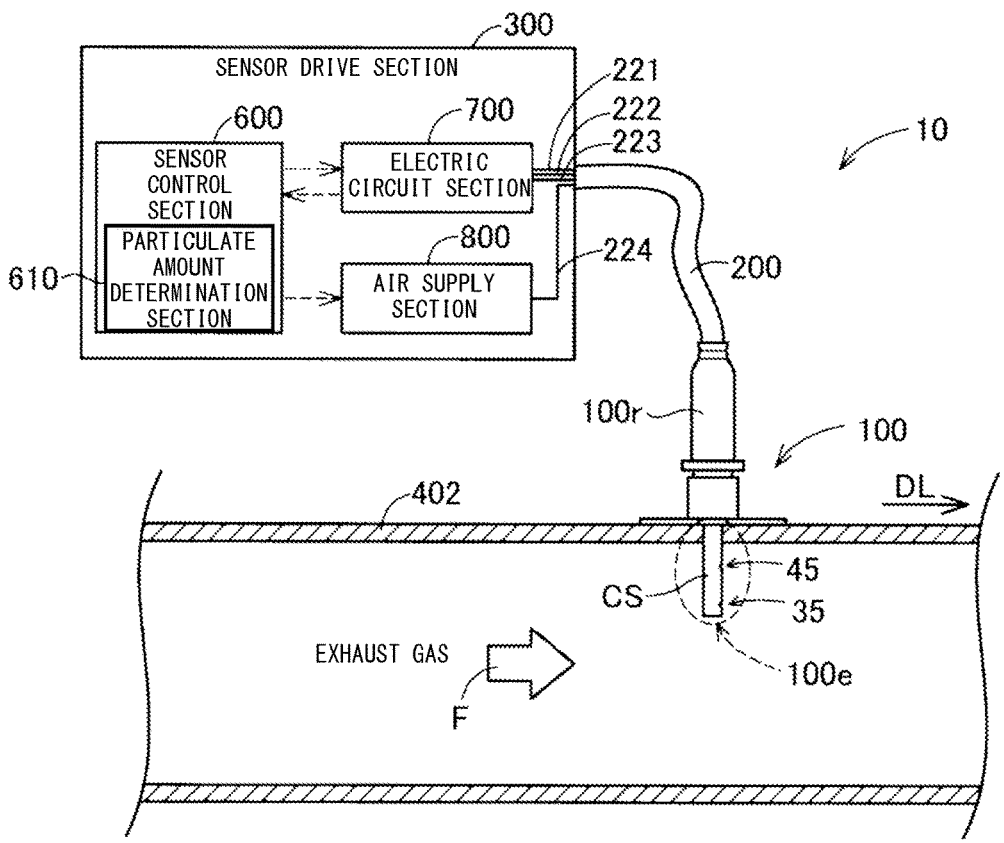

A. Configuration of Apparatus:

FIG. 1(a) is an explanatory view schematically showing the configuration of a vehicle 500 on which a particulate measurement system 10 is mounted. FIG. 1(b) is an explanatory view schematically showing the configuration of the particulate measurement system 10 attached to the vehicle 500. The particulate measurement system 10 includes a particulate sensor 100, a cable 200 and a sensor drive section 300, and measures the amount of particulates such as soot contained in exhaust gas discharged from an internal combustion engine 400. The internal combustion engine 400, which is a power source of the vehicle 500, is a diesel engine or the like. The vehicle 500 has various types of sensors 406 provided at different locations within the vehicle 500 in addition to the particulate sensor 100. Measured values of various operating condition parameters are supplied from these sensors 406 to a vehicle control section 420. Examples of the operating condition parameters include speed of the vehicle 500, rotational speed of internal combustion engine 400, torque of the internal combustion engine 400, exhaust gas temperature of the internal combustion engine 400, exhaust pressure of the internal combustion engine 400, intake pressure of the internal combustion engine 400, EGR opening degree (in the case where an EGR valve (Exhaust Gas Recirculation valve) is provided), amount of air taken into the internal combustion engine 400, fuel injection amount and ignition timing, etc. Each of these operating condition parameters is a parameter which is considered to affect the amount, size, etc., of particulates contained in the exhaust gas. Of these parameters, at least one of three operating condition parameters which are the speed of the vehicle 500, the rotational speed of internal combustion engine 400, and the torque of the internal combustion engine 400 which will be described below is considered to be likely to affect the amount, size, etc., of particulates contained in the exhaust gas.

The particulate sensor 100 is attached to an exhaust gas pipe 402 extending from the internal combustion engine 400, and is electrically connected to the sensor drive section 300 through the cable 200. In the present embodiment, the particulate sensor 100 is attached to the exhaust gas pipe 402 located downstream of a filter apparatus 410 (e.g., a DPF (diesel particulate filter)). The particulate sensor 100 outputs to the sensor drive section 300 a signal which correlates with the amount of particulates contained in the exhaust gas.

The sensor drive section 300 drives the particulate sensor 100 and measures the amount of particulates contained in the exhaust gas based on the signal supplied from the particulate sensor 100. In the present embodiment, "the amount of particulates" is measured as a value proportional to the total of the masses of particulates contained in the exhaust gas. However, "the amount of particulates" may be measured as a value proportional to the total of the surface areas of the particulates or a value proportional to the number of particulates contained in a unit volume of the exhaust gas. The sensor drive section 300 outputs to the vehicle control section 420 a signal representing the detected amount of particulates contained in the exhaust gas. In accordance with the signal supplied from the sensor drive section 300, the vehicle control section 420 controls the combustion state of the internal combustion engine 400, the amount of fuel supplied from a fuel supply section 430 to the internal combustion engine 400 through a fuel pipe 405, etc. The vehicle control section 420 may be configured to warn a driver of the vehicle 500 of deterioration or anomaly of the filter apparatus 410, for example, when the amount of particulates in the exhaust gas is greater than a predetermined upper limit (threshold). Electric power is supplied from a power supply section 440 to the sensor drive section 300 and the vehicle control section 420.

As shown in FIG. 1(b), the particulate sensor 100 has a cylindrical forward end portion 100e, and is fixed to the outer surface of the exhaust gas pipe 402 such that the forward end portion 100e is inserted into the exhaust gas pipe 402. In the present embodiment, the forward end portion 100e of the particulate sensor 100 is inserted approximately perpendicular to an extension direction DL of the exhaust gas pipe 402. A casing CS of the forward end portion 100e has an inflow hole 45 and a discharge hole 35 formed on the surface of the casing CS. The inflow hole 45 is used to introduce the exhaust gas into the interior of the casing CS, and the discharge hole 35 is used to discharge the introduced exhaust gas to the outside of the casing CS. A portion of the exhaust gas flowing through the exhaust gas pipe 402 is introduced into the interior of the casing CS of the forward end portion 100e through the inflow hole 45. Particulates contained in the introduced exhaust gas are electrified by ions (positive ions in the present embodiment) generated by the particulate sensor 100. The exhaust gas containing the electrified particulates is discharged to the outside of the casing CS through the discharge hole 35. The internal structure of the casing CS and the specific structure of the particulate sensor 100 will be described below.

The cable 200 is attached to a rear end portion 100r of the particulate sensor 100. The cable 200 includes a first wiring line 221, a second wiring line 222, a signal line 223 and an air supply tube 224 bundled together. The first wiring line 221, the second wiring line 222 and the signal line 223 are electrically connected to the sensor drive section 300. The air supply tube 224 is connected to an air supply section 800.

The sensor drive section 300 includes a sensor control section 600, an electric circuit section 700 and the air supply section 800. Electrical connection is established between the sensor control section 600 and the electric circuit section 700 and between the sensor control section 600 and the air supply section 800.

The sensor control section 600 includes a microcomputer, and controls the electric circuit section 700 and the air supply section 800. Also, the sensor control section 600 includes a particulate amount determination section 610 which determines the amount of particulates contained in the exhaust gas from a signal supplied from the electric circuit section 700. The particulate amount determination section 610 outputs to the vehicle control section 420 a signal representing the amount of particulates contained in the exhaust gas.

The electric circuit section 700 supplies electric power to the particulate sensor 100 through the first wiring line 221 and the second wiring line 222 so as to drive the particulate sensor 100. A signal which correlates with the amount of particulates contained in the exhaust gas is supplied from the particulate sensor 100 to the electric circuit section 700 through the signal line 223. Using this signal supplied through the signal line 223, the electric circuit section 700 outputs to the sensor control section 600 a signal corresponding to the amount of particulates contained in the exhaust gas. These signals will be described in detail below.

The air supply section 800 includes a pump (not shown), and supplies high-pressure air to the particulate sensor 100 through the air supply tube 224 in response to an instruction from the sensor control section 600. The high-pressure air supplied from the air supply section 800 is used for measurement of the amount of particulates by the particulate sensor 100. Notably, instead of supplying air from the air supply section 800, another type of gas may be supplied to the particulate sensor 100.

Figure 2:
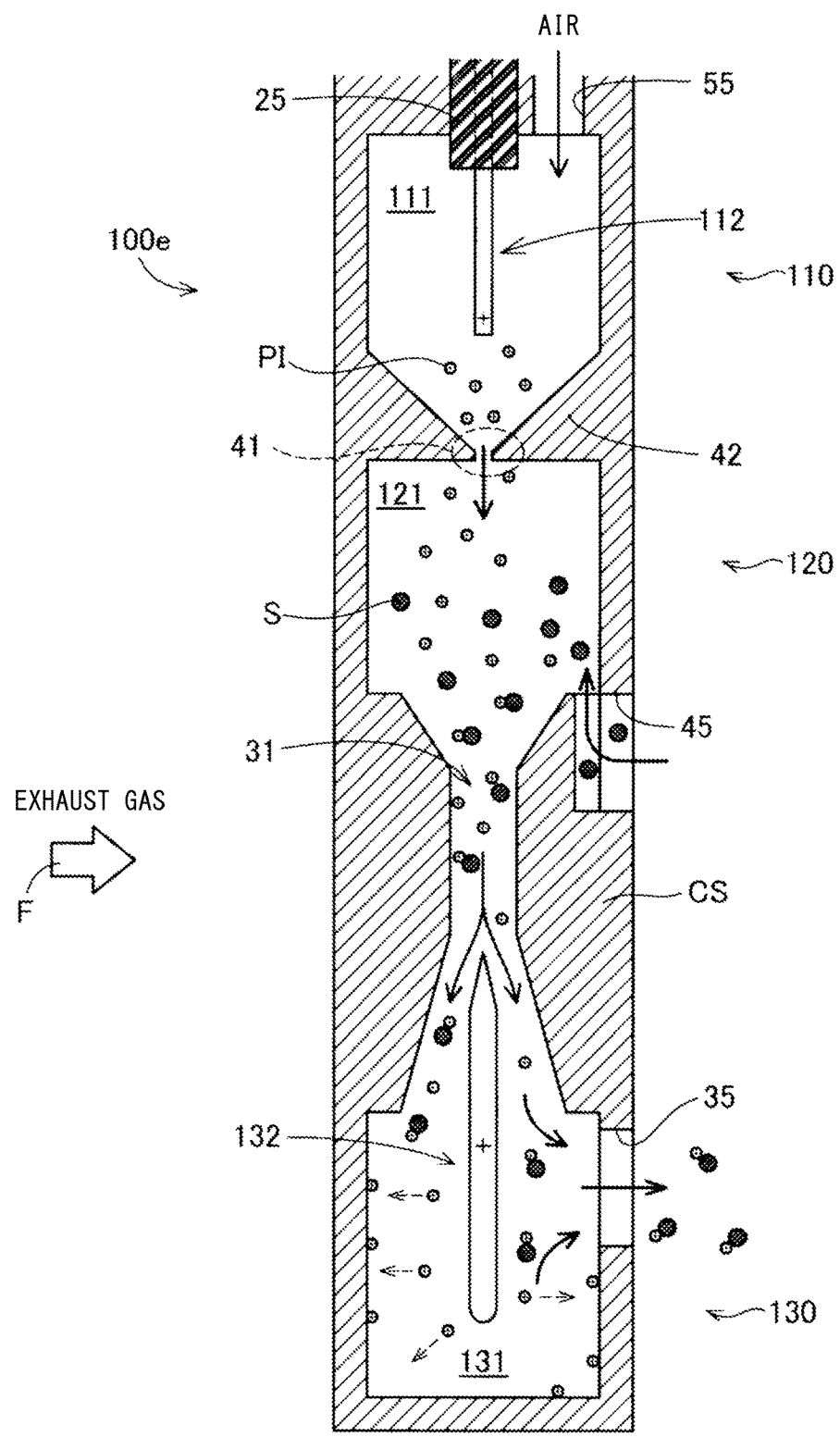
FIG. 2 is an explanatory view showing the configuration of a forward end portion of a particulate sensor.

FIG. 2 is an external view schematically showing the structure of the forward end portion 100e of the particulate sensor 100. The forward end portion 100e includes an ion generation section 110, an exhaust gas electrification section 120 and an ion trapping section 130 which are provided in the casing CS. Namely, within the casing CS, these three processing sections 110, 120 and 130 are arranged in this order, along the axial direction of the particulate sensor 100, from the base end side (the upper side in FIG. 2) of the forward end portion 100e toward the forward end side (the lower side in FIG. 2) thereof. The casing CS is formed of an electrically conductive material, and is connected to a secondary-side ground SGL (FIG. 3) through the signal line 223 (FIG. 1).

The ion generation section 110 is a processing section for generating ions (positive ions in the present embodiment) which are supplied to the exhaust gas electrification section 120. The ion generation section 110 includes an ion generation chamber 111 and a first electrode 112. The ion generation chamber 111 is a small space formed inside the casing CS. An air supply hole 55 and a nozzle 41 are provided on the inner circumferential surface of the ion generation chamber 111. The first electrode 112 is attached such that it projects into the ion generation chamber 111. The air supply hole 55 communicates with the air supply tube 224 (FIG. 1), and the high-pressure air supplied from the air supply section 800 (FIG. 1) is supplied to the ion generation chamber 111 through the air supply hole 55. The nozzle 41 is a very small hole (orifice) provided near the center of a partition wall 42 provided between the ion generation chamber 111 and the exhaust gas electrification section 120. The nozzle 41 supplies the ions generated in the ion generation chamber 111 to an electrification chamber 121 of the exhaust gas electrification section 120. The first electrode 112 has a rod-like outer shape, and its base end portion is fixed to the casing CS via a ceramic pipe 25 in a state in which a forward end portion of the first electrode 112 is located near the partition wall 42. The first electrode 112 is connected to the electric circuit section 700 (FIG. 1) through the first wiring line 221 (FIG. 1).

Using the electric power supplied from the electric circuit section 700, the ion generation section 110 applies a DC voltage (e.g., 2 to 3 kV) between the first electrode 112 (positive pole) and the partition wall 42 (negative pole). Through application of this voltage, the ion generation section 110 produces a corona discharge between a forward end portion of the first electrode 112 and the partition wall 42 to thereby generate positive ions PI. The positive ions PI generated in the ion generation section 110 are jetted into the electrification chamber 121 of the exhaust gas electrification section 120 through the nozzle 41 together with the high-pressure air supplied from the air supply section 800 (FIG. 1). Preferably, the jetting speed of air jetted from the nozzle 41 is set to a speed near the speed of sound.

The exhaust gas electrification section 120 is a section for electrifying particulates contained in the exhaust gas by positive ions PI, and includes the above-mentioned electrification chamber 121. The electrification chamber 121 is a small space located adjacent to the ion generation chamber 111, and communicates with the ion generation chamber 111 through the nozzle 41. Also, the electrification chamber 121 communicates with the outside of the casing CS through the inflow hole 45, and communicates with a trapping chamber 131 of the ion trapping section 130 through a gas flow passage 31. The electrification chamber 121 is configured such that, when air containing the positive ions PI are jetted from the nozzle 41, a negative pressure is created in the electrification chamber 121, and the exhaust gas located outside the casing CS flows into the electrification chamber 121 through the inflow hole 45. The air injected from the nozzle 41 and containing the positive ions PI and the exhaust gas flowing inward through the inflow hole 45 are mixed together within the electrification chamber 121. At that time, at least a portion of the particulates S contained in the exhaust gas that have flowed inward through the inflow hole 45 are electrified by the positive ions PI supplied from the nozzle 41 (i.e., the positive ions PI adhere to at least a portion of the particulates S). The air containing the electrified particulates S and the positive ions PI not used for electrification is supplied to the trapping chamber 131 of the ion trapping section 130 through a gas flow passage 31.

The ion trapping section 130 is a section for trapping ions not used for electrification of the particulates S, and includes the above-mentioned trapping chamber 131 and a second electrode 132. The trapping chamber 131 is a small space located adjacent to the electrification chamber 121, and communicates with the electrification chamber 121 through a gas flow passage 31. Also, the trapping chamber 131 communicates with the outside of the casing CS through the discharge hole 35. The second electrode 132 has a generally rod-like outer shape and has a tapered upper end. The second electrode 132 is fixed to the casing CS such that its longitudinal direction coincides with the flow direction of air flowing through the gas flow passage 31 (the extending direction of the casing CS). The second electrode 132 is connected to the electric circuit section 700 (FIG. 1) through the second wiring line 222 (FIG. 1). The second electrode 132 functions as an auxiliary electrode to which a voltage of about 100 V is applied and which assists the operation of trapping positive ions not used for electrification of particulates S. Specifically, a voltage is applied to the ion trapping section 130 such that the second electrode 132 serves as a positive pole, and the casing CS constituting the electrification chamber 121 and the trapping chamber 131 serves as a negative pole. As a result, the positive ions PI not used for electrification of particulates S (such positive ions PI will be referred to as "free positive ions") receive a repulsive force from the second electrode 132, whereby their advancing directions deviate to directions away from the second electrode 132. The positive ions PI whose advancing directions have been deviated are trapped by the inner circumferential walls of the trapping chamber 131 and the gas flow passage 31 which function as a negative pole. Meanwhile, the particulates S to which positive ions PI have adhered also receive the repulsive force from the second electrode 132 as in the case of the free positive ions PI. However, since the particulates S are larger in mass than the free positive ions PI, the degree of deviation by the repulsive force is small as compared with the case of the free positive ions PI. Therefore, the electrified particulates S are discharged to the outside of the casing CS through the discharge hole 35 as a result of the flow of the exhaust gas.

The particulate sensor 100 outputs a signal showing a change in current which corresponds to the amount of positive ions PI trapped in the ion trapping section 130. The sensor control section 600 (FIG. 1) determines the amount of particulates S contained in the exhaust gas from the signal output from the particulate sensor 100. A method of determining the amount of particulates S contained in the exhaust gas from the signal output from the particulate sensor 100 will be described below.

Figure 3:
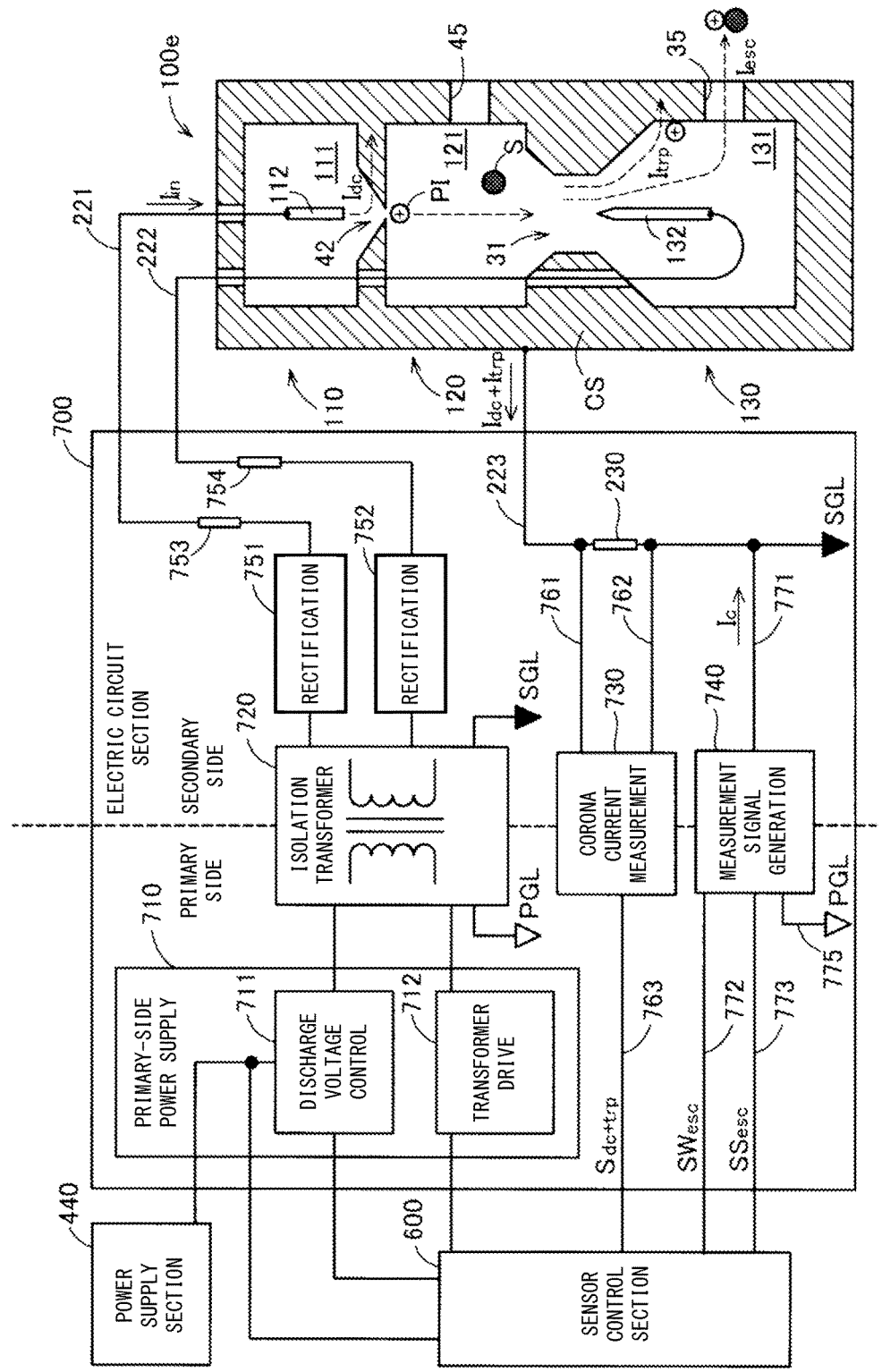
FIG. 3 is a block diagram showing the configuration of an electric circuit section.

FIG. 3 is a block diagram schematically showing the configuration of the electric circuit section 700. The electric circuit section 700 includes a primary-side power supply circuit 710, an isolation transformer 720, a corona current measurement circuit 730, a measurement signal generation circuit 740, a first rectification circuit 751, and a second rectification circuit 752.

The primary-side power supply circuit 710 steps up a DC voltage supplied from the power supply section 440, supplies the stepped up voltage to the isolation transformer 720, and drives the isolation transformer 720. The primary-side power supply circuit 710 includes a discharge voltage control circuit 711 and a transformer drive circuit 712. The discharge voltage control circuit 711 includes a DC/DC converter. Under control of the sensor control section 600, the discharge voltage control circuit 711 can arbitrarily change the voltage supplied to the isolation transformer 720. The supplied voltage is controlled, for example, such that an input current supplied to the first electrode 112 of the particulate sensor 100 through the first wiring line 221 becomes equal to a previously set target current (e.g., 5 µA). The method of this control will be described below. As a result, the amount of positive ions PI generated by the corona discharge in the ion generation section 110 can be made constant.

The transformer drive circuit 712 includes a switch circuit which can switch the flow direction of current flowing through the primary-side coil of the isolation transformer 720. The transformer drive circuit 712 drives the isolation transformer 720 by a switching operation of the switch circuit. In the present embodiment, the transformer drive circuit 712 is a push-pull circuit. However, the transformer drive circuit 712 may be another type of circuit such as a half bridge circuit and a full bridge circuit.

The isolation transformer 720 performs voltage conversion for the electric power supplied from the primary-side power supply circuit 710, and supplies the voltage-converted electric power (AC electric power in the present embodiment) to rectification circuits 751 and 752 on the secondary side. The configuration of the secondary-side coil allows the isolation transformer 720 to set different amplification factors for the electric power supplied to the first rectification circuit 751 and for the electric power supplied to the second rectification circuit 752. The isolation transformer 720 of the present embodiment is configured such that the primary-side coil and the secondary-side coil are not in physical contact with each other but are magnetically coupled with each other. A circuit on the primary side of the isolation transformer 720 includes the sensor control section 600 and the power supply section 440 as well as the primary-side power supply circuit 710. A circuit on the secondary side of the isolation transformer 720 includes the particulate sensor 100 and the rectification circuits 751 and 752. The corona current measurement circuit 730 and the measurement signal generation circuit 740 are provided between the circuit on the primary side of the isolation transformer 720 and the circuit on the secondary side of the isolation transformer 720, and are electrically connected to the primary-side and secondary-side circuits, respectively. As described below, the corona current measurement circuit 730 is configured such that a circuit portion electrically connected to the circuit on the primary side of the isolation transformer 720 is physically insulated from a circuit portion electrically connected to the circuit on the secondary side of the isolation transformer 720. Here, a ground (ground potential) which serves as a reference potential of the primary-side circuit is referred to as a "primary-side ground PGL," and a ground which serves as a reference potential of the secondary-side circuit is referred to as a "secondary-side ground SGL." An end of the primary-side coil of the isolation transformer 720 is connected to the primary-side ground PGL, and an end of the secondary-side coil thereof is connected to the secondary-side ground SGL. The casing CS of the particulate sensor 100 is connected to the secondary-side ground SGL through the signal line 223 and a shunt resistor 230.

Each of the rectification circuits 751 and 752 converts the AC electric power output from the isolation transformer 720 to a DC electric power. The first rectification circuit 751 is connected to the first electrode 112 of the particulate sensor 100 through the first wiring line 221 and a resistor 753 for short protection. The DC voltage supplied from the first rectification circuit 751 is approximately equal to the discharge voltage at the first electrode 112 of the particulate sensor 100, and the DC current supplied from the first rectification circuit 751 is the same as the input current input to the first electrode 112. The second rectification circuit 752 is connected to the second electrode 132 of the particulate sensor 100 through the second wiring line 222 and a resistor 754 for short protection.

The corona current measurement circuit 730 is connected to the opposite ends of the shunt resistor 230 on the signal line 223 through wiring lines 761 and 762, and is connected to the sensor control section 600 through a wiring line 763. The corona current measurement circuit 730 outputs to the sensor control section 600 a signal $S_{dc+trp}$ representing a current $(I_{dc}+I_{trp})$ flowing from the casing CS toward the secondary-side ground SGL through the signal line 223. Here, a "signal representing a current" is not limited to a signal which directly represents the current, and may be a signal which indirectly represents the current. For example, the "signal representing a current" may be a signal on the basis of which the current can be specified by applying a computation expression or a map to information obtained from the signal.

As shown in Equation (1) described below, the current value of the current $(I_{dc}+I_{trp})$ flowing through the signal line 223 is approximately equal to the current value of the input current $I_{in}$. This is because a leakage current $I_{esc}$ in Equation (1) is about $1/10^6$ as large as the current $(I_{dc}+I_{trp})$ flowing through the signal line 223, and can be substantively disregarded in observing a change in the input current $I_{in}$. The current value of the input current is equal to the current value of the corona current of the ion generation unit 110, so that the current value of the current $(I_{dc}+I_{trp})$ flowing through the signal line 223 is approximately equal to the current value of the corona current. Therefore, the corona current measurement circuit 730 outputs the signal $S_{dc+trp}$ indicating the current value of the corona current of the ion generation unit 110 to the sensor control unit 600.

In accordance with the signal $S_{dc+trp}$ supplied from the corona current measurement circuit 730, the sensor control section 600 controls the discharge voltage control circuit 711 such that the input current $I_{in}$ becomes equal to a target current. Namely, the corona current measurement circuit 730 and the sensor control section 600 constitute a constant current circuit for rendering the corona current (=input current $I_{in}$) constant. Since the corona current correlates with the amount of positive ions PI generated in the ion generation section 110, the amount of positive ions PI generated in the ion generation section 110 is maintained at a fixed amount by this constant current circuit.

The measurement signal generation circuit 740 measures a current $I_c$ which corresponds to the current Iesc of positive ions PI which have flowed to the outside without being trapped in the ion trapping section 130 (hereinafter referred to as a "leakage current $I_{esc}$"). The measurement signal generation circuit 740 is connected to the signal line 223 on the secondary side through a wiring line 771, and is connected to the sensor control section 600 on the primary side through wiring lines 772 and 773. Also, the measurement signal generation circuit 740 is connected to the primary-side ground PGL through a wiring line 775. The measurement signal generation circuit 740 outputs a low-sensitivity measurement signal $SW_{esc}$ to the sensor control section 600 through the wiring line 772, and outputs a high-sensitivity measurement signal $SS_{esc}$ to the sensor control section 600 through the wiring line 773. Notably, it is unnecessary to produce both the low-sensitivity measurement signal $SW_{esc}$ and the high-sensitivity measurement signal $SS_{esc}$. The measurement signal generation circuit 740 may be modified to produce one of these measurement signals (for example, the high-sensitivity measurement signal $SS_{esc}$) only, and to supply the generated signal to the sensor control section 600.

Currents flowing through the forward end portion 100e of the particulate sensor 100 satisfy the following relational expression (1).

$$I_{in}=I_{dc}+I_{trp}+I_{esc} \quad (1)$$

In this expression, $I_{in}$ is a current input to the first electrode 112, $I_{dc}$ is a discharge current flowing to the casing CS through the partition wall 42, $I_{trp}$ is a trap current corresponding to the amount of charge of positive ions PI trapped by the casing CS, and $I_{esc}$ is a leakage current corresponding to the amount of charge of positive ions PI having flowed to the outside without being trapped in the ion trapping section 130.

Since the discharge current $I_{dc}$ and the trap current $I_{trp}$ flow from the casing CS to the secondary-side ground SGL through the signal line 223, a current $(I_{dc}+I_{trp})$ which is the sum of these currents flows through the shunt resistor 230 on the signal line 223. Meanwhile, as described above, the input current $I_{in}$ is controlled to a constant level by the constant current circuit. Accordingly, the leakage current $I_{esc}$ is equal to the difference between the input current $I_{in}$ and the current $(I_{dc}+I_{trp})$ flowing through the shunt resistor 230.

$$I_{esc}=I_{in}-(I_{dc}+I_{trp}) \qquad (2)$$

A current $I_c$ corresponding to the leak current $I_{esc}$ flows through the measurement signal generation circuit 740. The measurement signal generation circuit 740 produces a measurement signal $SS_{esc}$ (or $SW_{esc}$) corresponding to the current $I_c$ and outputs the measurement signal $SS_{esc}$ (or $SW_{esc}$) to the sensor control section 600. The particulate amount determination section 610 of the sensor control section 600 determines the amount of particulates contained in the exhaust gas on the basis of the measurement signal $SS_{esc}$ (or $SW_{esc}$). At that time, the particulate amount determination section 610 performs a correction which will be described below.

Figure 4:
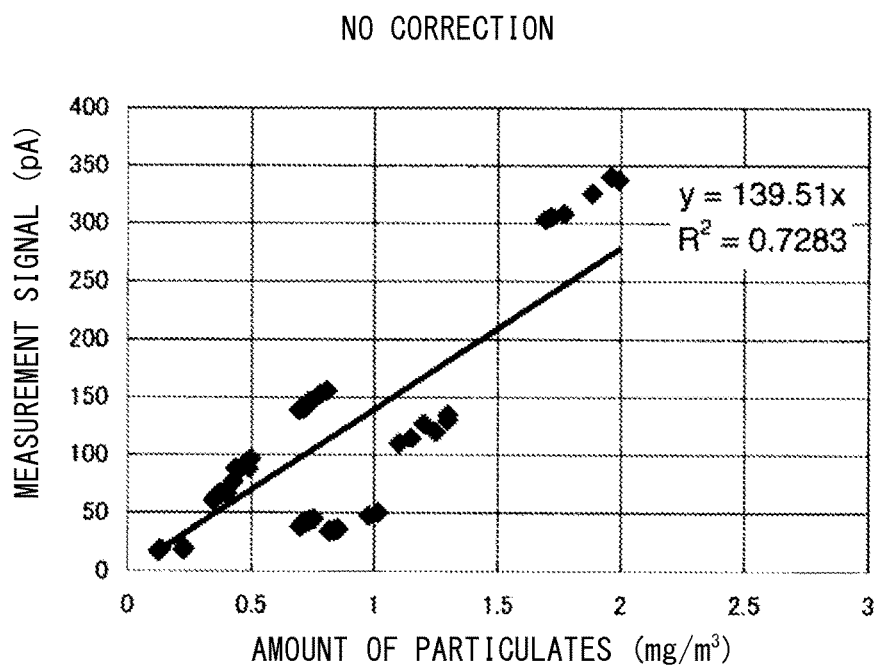
FIG. 4 is a graph showing the relation between a measurement signal and the amount of particulates before correction.

B. Correction of Measurement Result on the Basis of Operating Conditions:

FIG. 4 is a graph showing an example of the relation of the amount of particulates contained in the exhaust gas and the measurement signal. The horizontal axis represents the amount of particulates contained in the exhaust gas, and the vertical axis represents the measurement signal $SS_{esc}$. Strictly speaking, the horizontal axis represents the particulate concentration of the exhaust gas (mg/m$^3$), and the vertical axis represents the current $I_c$ (pA) corresponding to the voltage level of the measurement signal $SS_{esc}$. The graph shows a first-order approximation $y=a \cdot x$ of all the plotted measurement points and the square of its coefficient of correlation R. In general, the larger the value of $R^2$ (namely, the closer to 1), the higher the degree of correlation. In this example, it is understood that the value of $R^2$ is about 0.7, and the degree of correlation between the parameters x and y is not so large.

Figure 5:
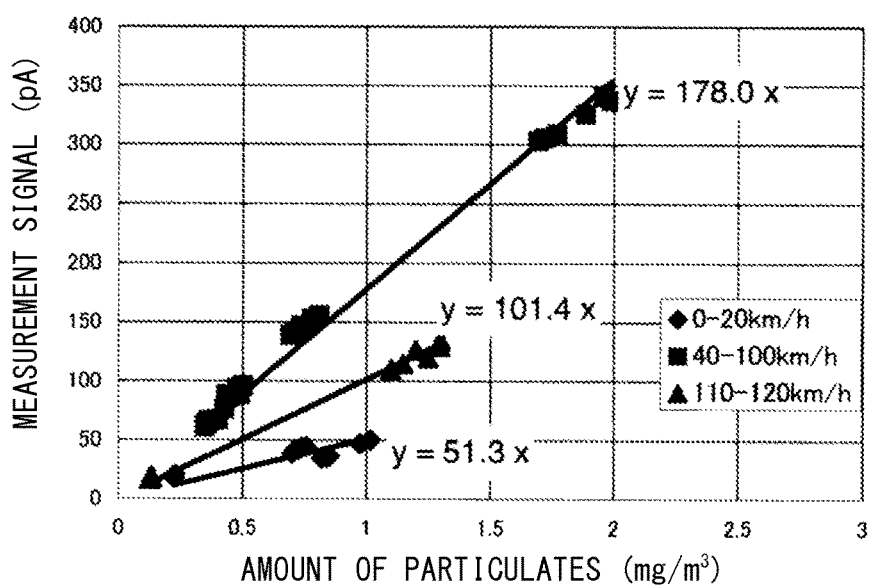
FIG. 5 is a graph in which the data of FIG. 4 is classified based on vehicle speed ranges.

FIG. 5 is a graph in which data shown in the graph of FIG. 4 is classified based on speed ranges of the vehicle 500. In the present embodiment, three speed ranges; i.e., 0 to 20 km/h, 40 to 100 km/h and 110 to 120 km/h, are used as the speed ranges of the vehicle 500. In a subset of measurement points in each of the three ranges, the degree of correlation between the amount of particulates and the measurement signal is greater than in FIG. 4. Presumably, the reason why the correlation between the amount of particulates and the measurement signal changes among the speed ranges of the vehicle 500 is that the diameter of particulates contained in the exhaust gas changes with the speed of the vehicle 500 as described below.

Figure 6:
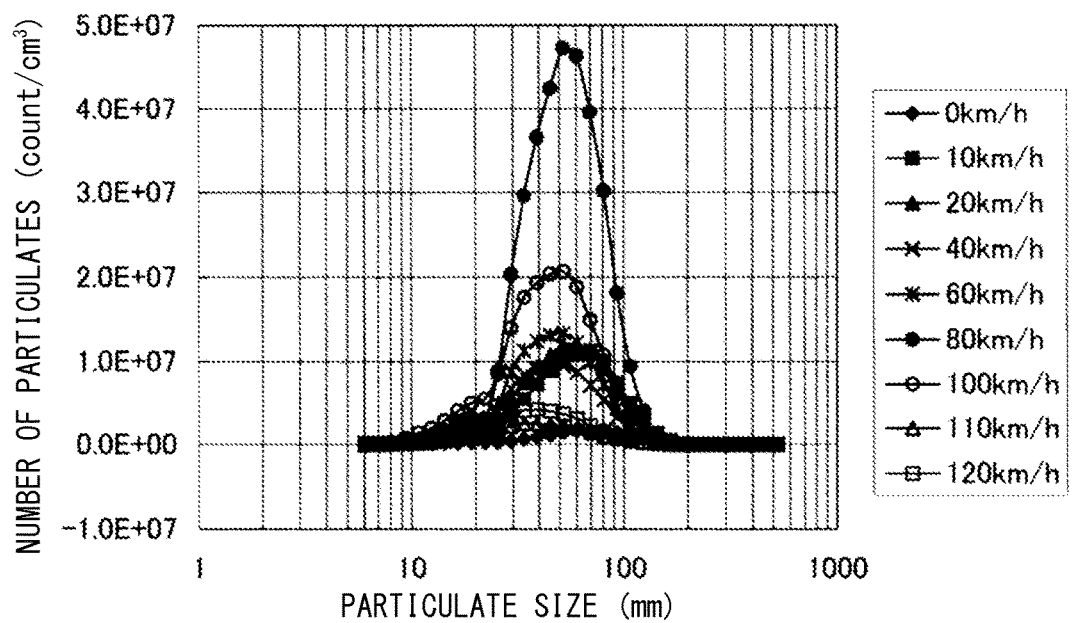
FIG. 6 is a graph showing the relation between vehicle speed and particulate size distribution of particulates.

FIG. 6 is a graph showing that the particulate size distribution of particulates contained in the exhaust gas changes with the speed of the vehicle 500. The horizontal axis represents the diameter (nm) of particulates, and the vertical axis represents the number of particulates (count/cm$^3$). As shown in this graph, the particulate size distribution changes with the speed of the vehicle 500, and the average of the particulate sizes also changes accordingly. Incidentally, the number of positive ions PI (FIG. 3) adhering to particulates presumably tends to increase with the surface area of each particulate. Meanwhile, the surface area of each particulate is proportional to the square of the particulate size, and the mass (weight) of each particulate is proportional to the cube of the particulate size. In the present embodiment, the amount of particulates associated with the measurement signal $SS_{esc}$ is the mass of particulates. Accordingly, when the average of particulate sizes changes with the speed of the vehicle 500, presumably, the relation between the signal level of the measurement signal $SS_{esc}$ and the mass of particulates also changes.

In view of the foregoing, in the present embodiment, the degree of correlation between the measurement signal $SS_{esc}$ and the amount of particulates is improved by correcting the measurement signal $SS_{esc}$ based on the speed of the vehicle 500. For example, this correction can be performed in accordance with the following equation.

$$y=y_0 \times \alpha(Vh) \qquad (3)$$

Here, y is a corrected measurement signal value, $y_0$ is a measurement signal value before correction, Vh is the vehicle speed, and $\alpha(Vh)$ is a coefficient determined in accordance with the vehicle Vh of the vehicle 500. The coefficient $\alpha(Vh)$ is a positive value which is not zero. Also, preferably, the coefficient $\alpha(Vh)$ assumes a value other than 1 for at least one value of the speed Vh.

Figure 7:
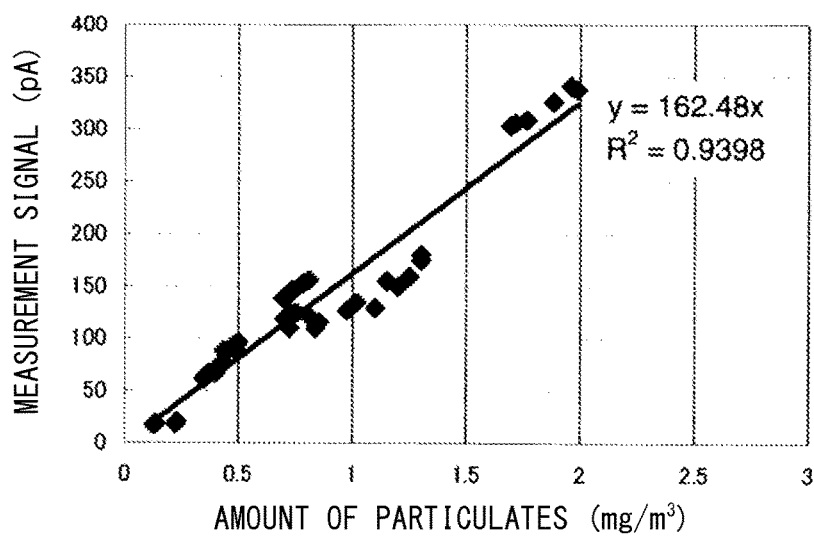
FIG. 7 is a graph showing the result of correction performed based on vehicle speed.

FIG. 7 is a graph showing the result of correction in which the speed correction by the above-described equation (3) was performed for all the measurement points of FIG. 4. It can be understood that as a result of this correction, the value of the square of the coefficient of correlation R becomes closer to 1 as compared with that shown in FIG. 4, and the degree of correlation between the parameters x and y (i.e., the amount of particulates and the measurement signal) increases considerably.

Figure 8:
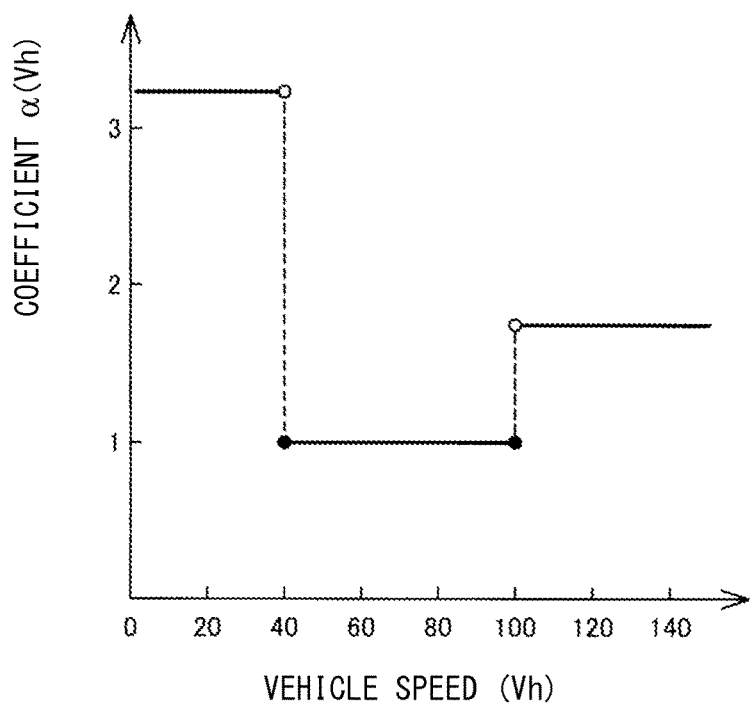
FIG. 8 is a graph showing a coefficient α which changes with vehicle speed serving as a parameter.

FIG. 8 shows the coefficient $\alpha(Vh)$ used for the correction of FIG. 7. As can be understood from this example, a step function which provides a fixed coefficient value for each of a plurality of ranges relating to the speed of the vehicle 500 can be used as a function which represents the coefficient $\alpha(Vh)$. However, a function other than a step function or a curve may be used so as to represent the coefficient $\alpha(Vh)$. Also, the division of the speed range of the vehicle 500 may be other than the division shown in FIG. 8. These points similarly apply to other operating condition parameters which will be described below.

Parameters other than the speed of the vehicle 500 may be used as operating condition parameters for correcting the measurement signal. For example, the measurement signal can be corrected using the rotational speed of the internal combustion engine 400 or the torque of the internal combustion engine 400.

Figure 9:
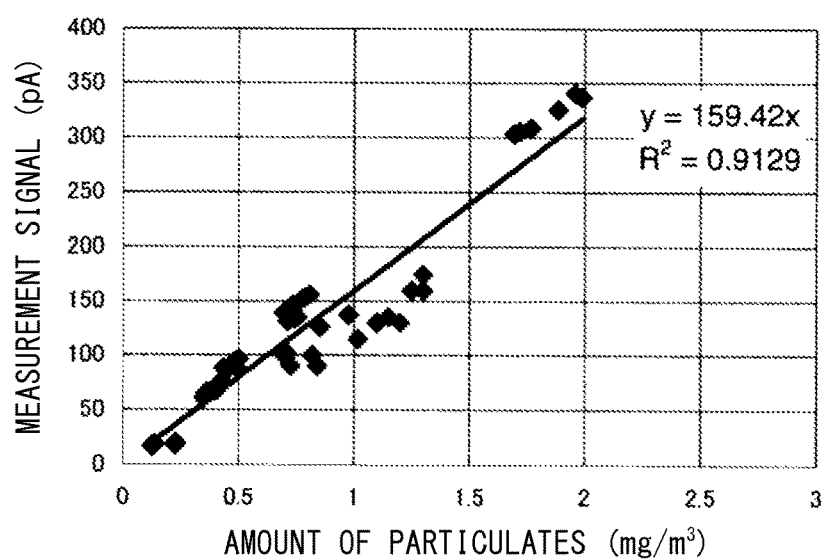
FIG. 9 is a graph showing the result of correction performed based on rotational speed of an internal combustion engine.
Figure 10:
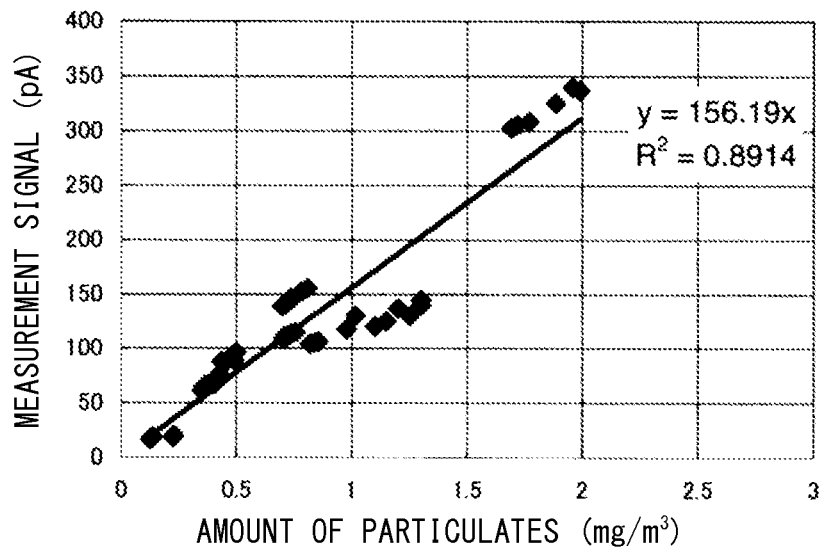
FIG. 10 is a graph showing the result of correction performed based on torque of the internal combustion engine.

FIG. 9 is a graph showing the result of correction in which correction was performed for all the measurement points of FIG. 4 in accordance with the rotational speed of the internal combustion engine 400. FIG. 10 is a graph showing the result of correction in which correction was performed for all the measurement points of FIG. 4 in accordance with the torque of the internal combustion engine 400. In each of FIGS. 9 and 10, the value of the square of the coefficient of correlation R becomes closer to 1 as compared with that shown in FIG. 4, and the degree of correlation between the parameters x and y increases considerably. Notably, an equation obtained by replacing the speed Vh of the vehicle 500 in the above-described equation (3) with the rotational speed of the internal combustion engine 400 or the torque of the internal combustion engine 400 can be used as an equation for correction.

Incidentally, the torque of the internal combustion engine 400 shows a large change within a single engine cycle (one cycle composed of two strokes or four strokes). Accordingly, the peak value of the torque measured by a torque sensor in each engine cycle can be used as a torque value used for correction of the measurement signal of the amount of particulates. This applies to other operating condition parameters (e.g., the exhaust pressure and intake pressure of the internal combustion engine 400) which change greatly within each engine cycle as in the case of torque. Notably, the average of torques measured by a torque sensor during each engine cycle may be used as a torque value used for correction of the measurement signal of the amount of particulates.

Figure 11:
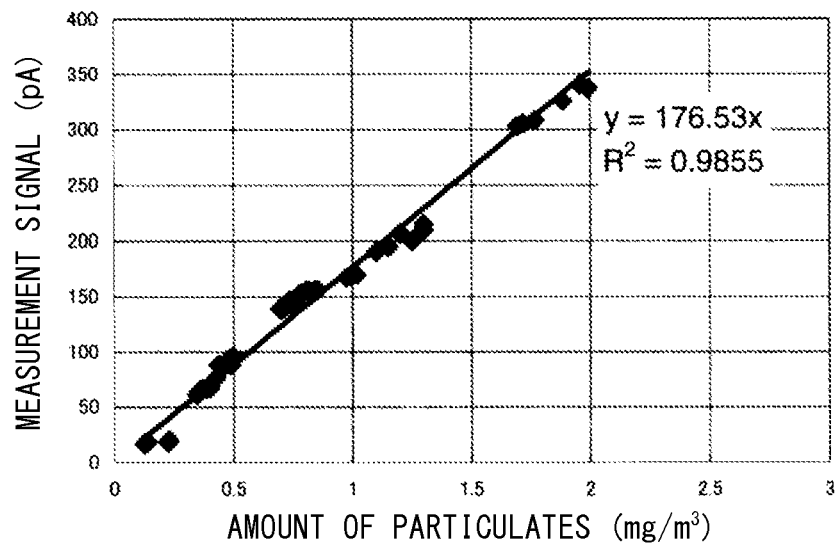
FIG. 11 is a graph showing the result of correction performed based on vehicle speed, rotational speed of the internal combustion engine and torque of the internal combustion engine.

FIG. 11 is a graph showing the result of correction in which correction was performed for all the measurement points of FIG. 4 in accordance with all the three parameters; i.e., the speed of the vehicle 500, the rotational speed of the internal combustion engine 400, and the torque of the internal combustion engine 400. The result of FIG. 11 shows that, as compared with the results shown in FIGS. 7, 9 and 10, the value of the square of the coefficient of correlation R becomes closer to 1 and the degree of correlation between the parameters x and y is considerably high. Notably, it is expected that, even in the case where correction is performed based on two of the above-described three parameters, measurement accuracy can be improved as compared with the case where correction is performed based on only one parameter.

For the correction based on the three parameters (the speed of the vehicle 500, the rotational speed of the internal combustion engine 400, and the torque of the internal combustion engine 400), for example, the following equation can be used.

$$y = y_0 \times \alpha(Vh) \times \beta(Neg) \times \gamma(Teg) \tag{4}$$

Here, y is a corrected measurement signal value, $y_0$ is a measurement signal value before correction, Vh is the speed of the vehicle 500, Neg is the rotational speed of the internal combustion engine 400, Teg is the torque of the internal combustion engine 400, and $\alpha(Vh)$, $\beta(Neg)$, and $\gamma(Teg)$ are coefficients determined in accordance with corresponding parameters Vh, Neg and Teg. Notably, each of the three coefficients $\alpha(Vh)$, $\beta(Neg)$ and $\gamma(Teg)$ is a positive value which is not zero. Also, the result of multiplication of the three coefficients $\alpha(Vh)$, $\beta(Neg)$ and $\gamma(Teg)$ preferably assumes a value other than 1 for at least one combination of the three parameters Vh, Neg and Teg. Notably, when equation (4) is used, it is possible to suppress loss of measurement accuracy through a simple correction.

Alternatively, correction may be performed using the following equation instead of the above-described equation (4).

$$y = y_0 \times \delta(Vh, Neg, Teg) \tag{5}$$

Here, y is a corrected measurement signal value, $y_0$ is a measurement signal value before correction, Vh is the speed of the vehicle 500, Neg is the rotational speed of the internal combustion engine 400, Teg is the torque of the internal combustion engine 400, and $\delta(Vh, Neg, Teg)$ is a coefficient determined in accordance with corresponding parameters Vh, Neg and Teg. The coefficient $\delta(Vh, Neg, Teg)$ is a positive value which is not zero. Also, the coefficient $\delta(Vh, Neg, Teg)$ preferably assumes a value other than 1 for at least one combination of the three parameters Vh, Neg and Teg. Notably, in the case where equation (5) is used, a lookup table having three inputs and one output which outputs the value of the coefficient $\delta(Vh, Neg, Teg)$ in accordance with the input values of the three parameters Vh, Neg and Teg is preferably provided in the sensor control section 600 in advance.

Alternatively, correction may be performed using the following equation instead of the above-described equation (4).

$$y = y_0 + \alpha(Vh) + \beta(Neg) + \gamma(Teg) \tag{6}$$

Notably, each of the three coefficients $\alpha(Vh)$, $\beta(Neg)$ and $\gamma(Teg)$ is a non-negative value, and at least one thereof is a positive value which is not zero. Notably, even in the case where this equation (6) is used, it is possible to suppress loss of measurement accuracy through a simple correction. However, from the viewpoint of measurement accuracy, the above-described equation (4) or (5) is preferably used rather than the equation (6).

As described above, in the present embodiment, correction of the measurement signal is performed on the basis of one or a plurality of operating condition parameters selected from the three operating condition parameters; i.e., the speed of the vehicle 500, the rotational speed of the internal combustion engine 400 and the torque of the internal combustion engine 400. Therefore, it is possible to perform accurate particulate measurement without excessively lowering the measurement accuracy even when the operating conditions change.

Notably, in the above-described embodiment, the measurement signal is corrected. However, the embodiment may be modified to correct the amount of particulates determined from the measurement signal. In this case as well, a correction equation can be used which is identical to equation (4) but in which y represents the corrected amount of particulates and $y_0$ represents the amount of particulates before correction. However, in this case, the values of the coefficients $\alpha(Vh)$, $\beta(Neg)$ and $\gamma(Teg)$ differ from those used when the measurement signal is corrected. These points also apply to the case where the above-described equation (5) or (6) is used.

Parameters other than the above-described three parameters may be used as operating condition parameters used for correction of the measurement signal or the amount of particulates. For example, operating condition parameters such as exhaust gas temperature of the internal combustion engine 400, exhaust pressure of the internal combustion engine 400, intake pressure of the internal combustion engine 400, EGR opening degree, amount of air taken into the internal combustion engine 400, fuel injection amount and ignition timing can be used. These operating condition parameters are considered to affect the amount, size, etc. of particulates contained in the exhaust gas.

C. Example of Configuration of Measurement Signal Generation Circuit

Figure 12:
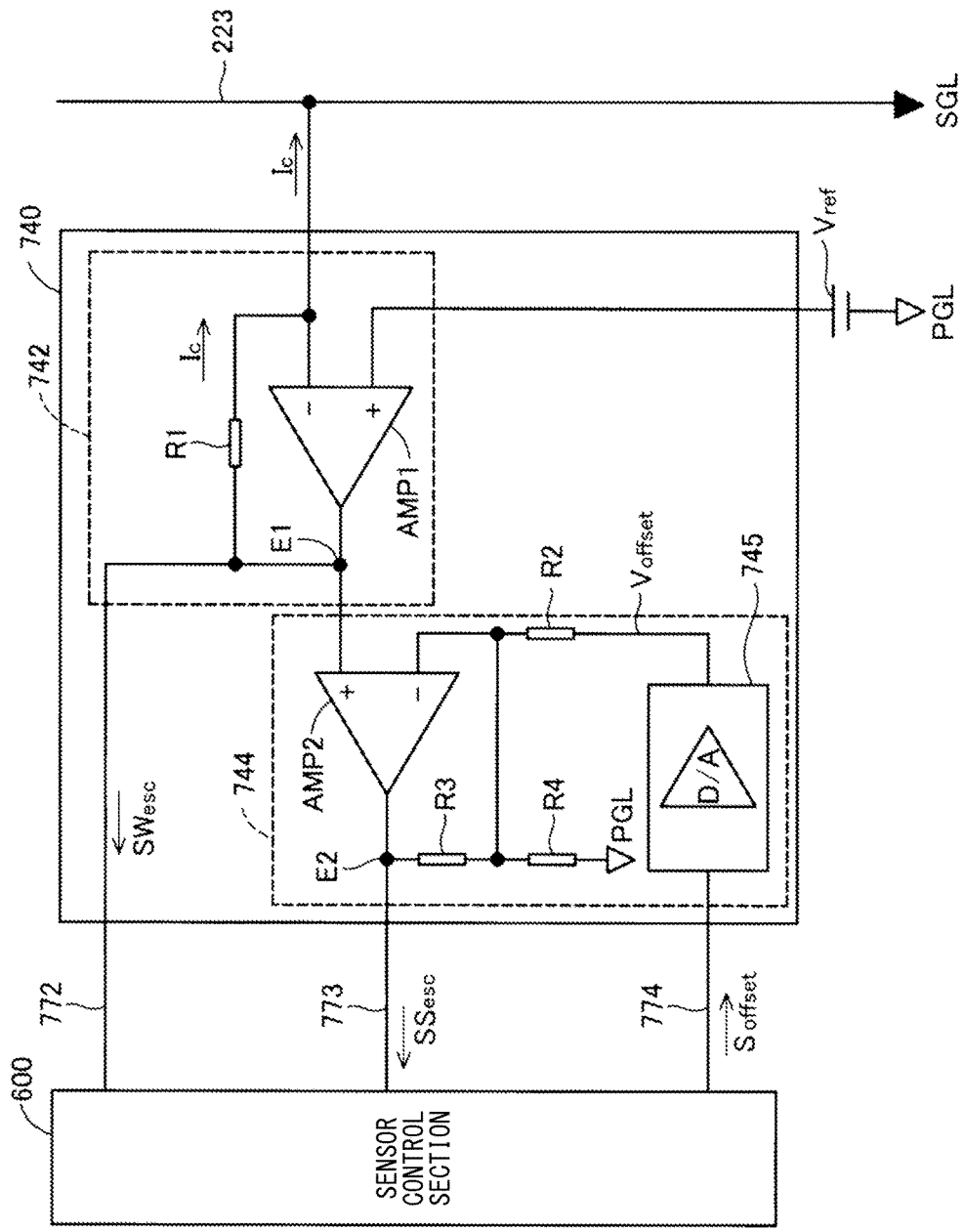
FIG. 12 is a block diagram showing the configuration of a measurement signal generation circuit.

FIG. 12 is a block diagram showing the configuration of the measurement signal generation circuit 740. The measurement signal generation circuit 740 includes an I-V conversion circuit 742 and a high-sensitivity measurement circuit 744 provided in a stage subsequent to the I-V conversion circuit 742. As described below, in the first embodiment, the I-V conversion circuit 742 functions as a low-sensitivity measurement circuit as well.

The I-V conversion circuit 742 includes a first amplification circuit AMP1 and a negative feedback resistor R1 therefor. An operational amplifier can be used as the first amplification circuit AMP1. The inverting input terminal of the first amplification circuit AMP1 is connected to the secondary-side ground SGL through the wiring line 223. As shown in FIG. 3, this wiring line 223 is connected to the casing CS of the particulate sensor. A power source $V_{ref}$ which provides a fixed reference voltage (e.g., 0.5 V) in relation to the primary-side ground PGL is connected to the non-inverting input terminal of the first amplification circuit AMP1. In the following description, the same symbol "$V_{ref}$" is used to represent the reference voltage of the power source $V_{ref}$. By inputting the reference voltage $V_{ref}$ to the non-inverting input terminal of the first amplification circuit AMP1, the potential difference between the two input terminals of the first amplification circuit AMP1 can be adjusted such that the potential difference approaches a potential difference range within which errors (e.g., errors caused by bias current and offset voltage) are less likely to be produced. As described in detail below, the current $I_c$ corresponding to the leakage current $I_{esc}$ (FIG. 3) of the particulate sensor 100 flows to the inverting input terminal of the first amplification circuit AMP1. This current $I_c$ is converted to a first voltage $E_1$ by the first amplification circuit AMP1. A signal $SW_{esc}$ representing the first voltage $E_1$ is supplied, as a low-sensitivity measurement signal, to the sensor control section 600 through the wiring line 772.

The reason why the current $I_c$ flowing to the inverting input terminal of the first amplification circuit AMP1 corresponds to the leakage current $I_{esc}$ of the particulate sensor 100 is as follows. When the leakage current $I_{esc}$ is generated, the reference potential of the secondary-side ground SGL becomes lower than the reference potential of the primary-side ground PGL in accordance with the magnitude of the leakage current $I_{esc}$. This is because a difference in energy corresponding to the leakage current $I_{esc}$ is produced between the energy (electric power) supplied from the primary-side circuit (including the primary-side power supply circuit 710 (FIG. 3)) to the particulate sensor 100 and the energy (electric power) output from the particulate sensor 100 through the signal line 223. When a difference is produced between the reference potential of the secondary-side ground SGL and the reference potential of the primary-side ground PGL as a result of generation of the leakage current $I_{esc}$, the compensation current $I_c$ corresponding to this difference flows to the inverting input terminal of the first amplification circuit AMP1. This compensation current $I_c$ is a current whose magnitude is equal to that of the leakage current $I_{esc}$ and which compensates for the difference between the reference potential of the secondary-side ground SGL and the reference potential of the primary-side ground PGL. Accordingly, the I-V conversion circuit 742 can produce the first voltage $E_1$ (and the low-sensitivity measurement signal $SW_{esc}$) representing the leakage current $I_{esc}$ by means of I-V conversion of the compensation current $I_c$.

The high-sensitivity measurement circuit 744 includes a second amplification circuit AMP2, three resistors R2, R3 and R4, and an offset voltage adjustment circuit 745. An operational amplifier can be used as the second amplification circuit AMP2. A non-inverting input terminal of the second amplification circuit AMP2 is connected to the output terminal of the I-V conversion circuit 742. An inverting input terminal of the second amplification circuit AMP2 is connected to an offset voltage adjustment circuit 745 through the resistor R2. A (digital) offset signal $S_{offset}$ having a signal level representing an offset voltage $V_{offset}$ is supplied from the sensor control section 600 to the offset voltage adjustment circuit 745 through the wiring line 774. The offset voltage adjustment circuit 745 converts (or decodes) the digital offset signal $S_{offset}$ to an analog offset voltage $V_{offset}$, outputs the offset voltage $V_{offset}$, and supplies it to the inverting input terminal of the second amplification circuit AMP2 through the resistor R2. The output terminal of the second amplification circuit AMP2 is connected to the primary-side ground PGL through the resistors R3 and R4. A node between these two resistors R3 and R4 is connected to the inverting input terminal of the second amplification circuit AMP2. Accordingly, the resistor R3 serves as a negative feedback resistor. This high-sensitivity measurement circuit 744 amplifies the output voltage $E_1$ of the I-V conversion circuit 742 and produces a voltage $E_2$. A signal $SS_{esc}$ representing the voltage $E_2$ is supplied, as a high-sensitivity measurement signal, to the sensor control section 600 through the wiring line 773.

The output voltages $E_1$ and $E_2$ of the two amplification circuits AMP1 and AMP2 are given by the following equations.

$$E1 = I_c \times R1 + V_{ref} \tag{7a}$$

$$E2 = \left(1 + \frac{R3}{R4}\right) \times E1 + \frac{R3}{R2} + E1 - \frac{R3}{R2} \times V_{offset} \tag{7b}$$

In these equations, $I_c$ is the compensation current, R1 through R4 are the resistances of the resistors R1 through R4, $V_{ref}$ is the reference voltage of the first amplification circuit AMP1, and $V_{offset}$ is the offset voltage of the second amplification circuit AMP2.

The amplification factor of the second amplification circuit AMP2 (i.e., the amplification factor of the high-sensitivity measurement circuit 744) can be adjusted by adjusting the resistances R2 through R4. For example, the amplification factor of the second amplification circuit AMP2 can be set to about 103 times. Also, as will be described below, the measurable range of the high-sensitivity measurement circuit 744 for the compensation current $I_c$ (i.e., the leakage current $I_{esc}$) (namely, a particulate amount measurement window) can be shifted by adjusting the offset voltage $V_{offset}$.

The sensor control section 600 determines the amount of particulates S contained in the exhaust gas based on the low-sensitivity measurement signal $SW_{esc}$ and the high-sensitivity measurement signal $SS_{esc}$ supplied from the measurement signal generation circuit 740. In order to determine the amount of particulates S contained in the exhaust gas from the measurement signal $SS_{esc}$ (or $SW_{esc}$), for example, a method of referring to a map which shows the relation between the voltage value of the measurement signal $SS_{esc}$ (or $SW_{esc}$) and the amount of particulates S contained in the exhaust gas or a method of using a relational expression which shows the relation between the voltage value of the measurement signal $SS_{esc}$ (or $SW_{esc}$) and the amount of particulates S contained in the exhaust gas can be used.

The sensor control section 600 converts each of the voltage values of the high-sensitivity measurement signal $SS_{esc}$ and the low-sensitivity measurement signal $SW_{esc}$, which are analog, to a digital value of a predetermined resolution (for example, 8 bits). Also, the sensor control section 600 is configured such that the size of the voltage readable range (the range of the full scale) becomes the same for the measurement signals $SS_{esc}$ and $SW_{esc}$.

The high-sensitivity measurement signal $SS_{esc}$ has a high sensitivity (resolution) for the leakage current $I_{esc}$ as compared with the low-sensitivity measurement signal $SW_{esc}$. For example, whereas a voltage level of the low-sensitivity measurement signal $SW_{esc}$ of 1 V corresponds to a magnitude of the leakage current $I_{esc}$ of 1 nA, a voltage level of the high-sensitivity measurement signal $SS_{esc}$ of 1 V corresponds to a magnitude of the leakage current $I_{esc}$ of 1 pA. Meanwhile, the sensor control section 600 has the same voltage resolution (the minimum recognizable voltage difference) (for example, 0.02 V) for both the measurement signals $SS_{esc}$ and $SW_{esc}$. Accordingly, the magnitude of the leakage current $I_{esc}$ corresponding to the voltage resolution of the sensor control section 600 is small for the case of the high-sensitivity measurement signal $SS_{esc}$ (e.g., 0.02 pA) and is large for the case of the low-sensitivity measurement signal $SW_{esc}$ (e.g., 0.02 nA). In other words, the sensor control section 600 can detect a smaller change in the leakage current $I_{esc}$ based on the high-sensitivity measurement signal $SS_{esc}$, as compared with the low-sensitivity measurement signal $SW_{esc}$. As can be understood from these explanations as well, in the present specification, the term "sensitivity" means the resolution or the minimum measurement unit. Namely, the term "high sensitivity" means that the minimum measurement unit for the amount of particulates is small, and the term "low sensitivity" means that the minimum measurement unit for the amount of particulates is large.

As described above, the amount of particulates contained in the exhaust gas obtained from the high-sensitivity measurement signal $SS_{esc}$ is smaller in the minimum recognizable unit and is higher in accuracy than the amount of particulates contained in the exhaust gas obtained from the low-sensitivity measurement signal $SW_{esc}$. Meanwhile, the readable voltage range (e.g., 0 to 5 V) of the sensor control section 600 is set to cover the entire voltage range of the low-sensitivity measurement signal $SW_{esc}$. Therefore, a range in which the amount of particulates contained in the exhaust gas can be measured based on the low-sensitivity measurement signal $SW_{esc}$ is wider than a range in which the amount of particulates contained in the exhaust gas can be measured based on the high-sensitivity measurement signal $SS_{esc}$. If the amount of particulates contained in the exhaust gas falls within a range corresponding to the entire voltage range of the low-sensitivity measurement signal $SW_{esc}$, the amount of particulates can be measured within the entire range.

Meanwhile, in the case where the high-sensitivity measurement signal $SS_{esc}$ is used, so long as the amount of particulates contained in the exhaust gas falls within a considerably narrow measurement window (measurement range), the sensor control section 600 can determine the amount of particulates. However, when the amount of particulates falls outside the measurement range, the sensor control section 600 becomes unable to determine the amount of particulates because it exceeds the voltage range of the second amplification circuit AMP2. In order to overcome such a drawback, in the first embodiment, as described in the following description of processing steps, the measurement window for measurement of the amount of particulates based on the high-sensitivity measurement signal $SS_{esc}$ is changed by changing the offset voltage $V_{offset}$ output from the offset voltage adjustment circuit 745 in accordance with the voltage level $E_1$ of the low-sensitivity measurement signal $SW_{esc}$.

Figure 13:
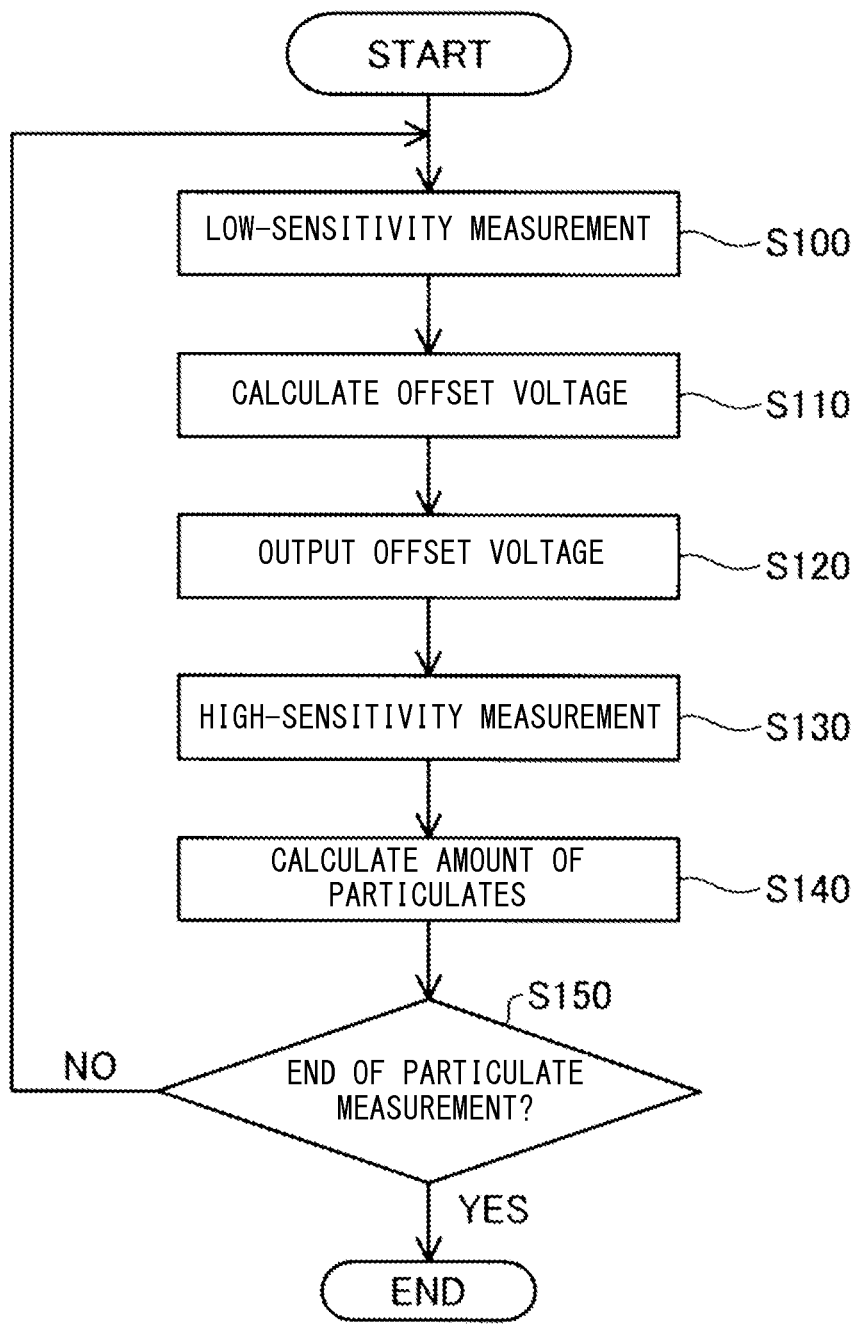
FIG. 13 is a flowchart showing steps of particulate measurement processing.

FIG. 13 is a flowchart showing steps of the particulate measurement processing in the first embodiment. When the particulate measurement processing is started, in step S100, low-sensitivity measurement is performed, and the sensor control section 600 receives the low-sensitivity measurement signal $SW_{esc}$. At that time, the sensor control section 600 may calculate or determine the amount of particulates based on the voltage level of the low-sensitivity measurement signal $SW_{esc}$. In step S110, the sensor control section 600 calculates the offset voltage $V_{offset}$ of the high-sensitivity measurement circuit 744 in accordance with the voltage level $E_1$ of the low-sensitivity measurement signal $SW_{esc}$. At that time, the offset voltage $V_{offset}$ is determined such that the output voltage $E_2$ of the high-sensitivity measurement circuit 744 output from the second amplification circuit AMP2 assumes a predetermined value (for example, the center value) within the output voltage range of the second amplification circuit AMP2. For example, in the case where the lower limit of the output voltage range of the second amplification circuit AMP2 is $V_{min}$ and the upper limit thereof is $V_{max}$, the offset voltage $V_{offset}$ can be calculated such that the output voltage $E_2$ becomes equal to $(V_{min}+V_{max})/2$. Calculation of such an offset voltage $V_{offset}$ can be performed using a known relational expression (e.g., the above-described equation (7b)) between the offset voltage $V_{offset}$ and the two voltages $E_1$ and $E_2$.

In step S120, the sensor control section 600 outputs to the offset voltage adjustment circuit 745 an offset signal $S_{offset}$ having a signal level representing the calculated offset voltage $V_{offset}$. The offset voltage adjustment circuit 745 converts (or decodes) the (digital) offset signal $S_{offset}$ to obtain an analog offset voltage $V_{offset}$, outputs the offset voltage $V_{offset}$, and supplies it to the inverting input terminal of the second amplification circuit AMP2 through the resistor R2. In step S130, high-sensitivity measurement is performed, and the sensor control section 600 receives the high-sensitivity measurement signal $SS_{esc}$. In step S140, the sensor control section 600 calculates or determines the amount of particulates based on the high-sensitivity measurement signal $SS_{esc}$. As described above, in the high-sensitivity measurement, the voltage level $E_2$ of the high-sensitivity measurement signal $SS_{esc}$ is determined to fall within the output voltage range of the second amplification circuit AMP2. Therefore, the sensor control section 600 can determine the amount of particulates with a high sensitivity in accordance with the high-sensitivity measurement signal $SS_{esc}$. In step S150, a determination is made as to whether or not the particulate measurement ends. The above-described steps S100 through S150 are repeatedly executed until the particulate measurement ends. The repetition intervals of the steps S100 through S150 can be set to, for example, 1 ms to 2 ms.

Figure 14:
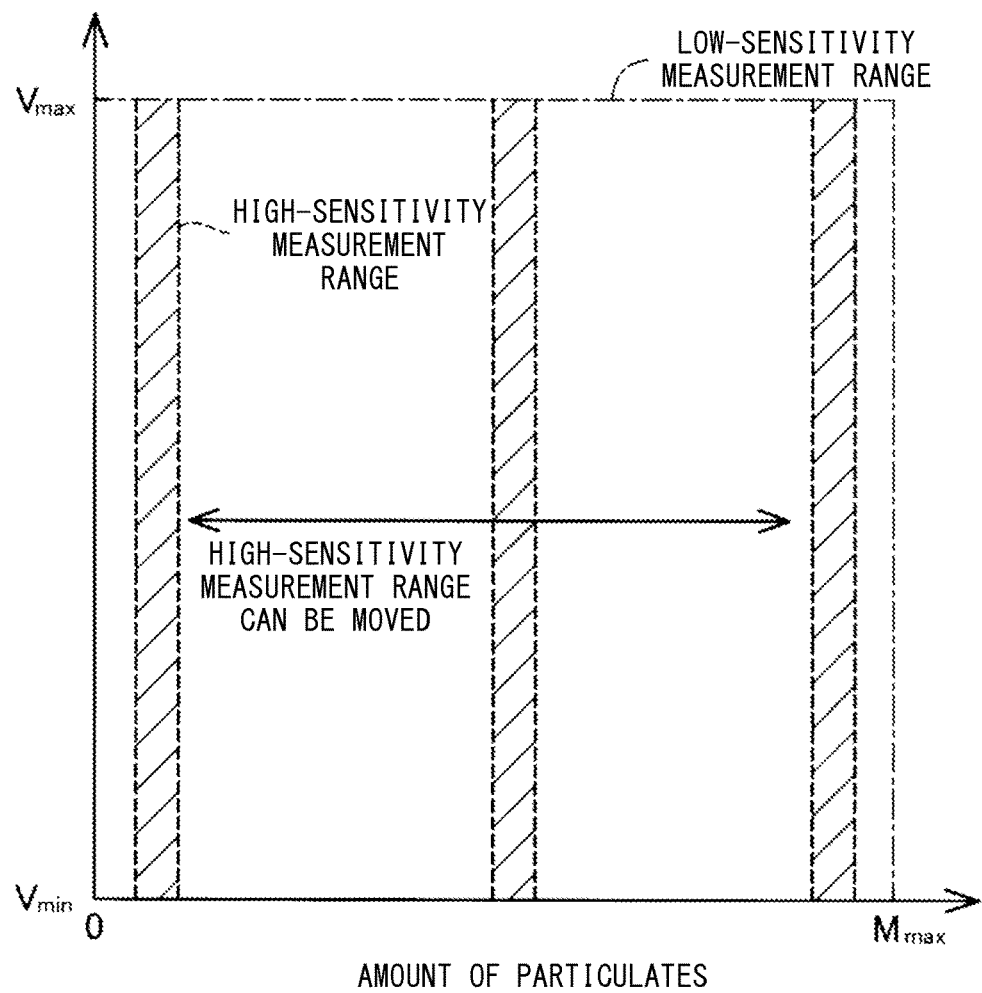
FIG. 14 is an explanatory illustration showing the relation between a low-sensitivity measurement range and a high-sensitivity measurement range.

FIG. 14 is an explanatory illustration showing the relation between a low-sensitivity measurement range and a high-sensitivity measurement range. The horizontal axis of FIG. 14 represents the amount of particulates, and the vertical axis thereof represents the output voltage level of the amplification circuits AMP1 and AMP2. The range of the amount of particulates in which the amount can be measured based on the low-sensitivity measurement signal $SW_{esc}$ (the measurement window for the low-sensitivity measurement) is a wide range extending from 0 to $M_{max}$. Meanwhile, the range of the amount of particulates in which the amount can be measured based on the high-sensitivity measurement signal $SS_{esc}$ (the measurement window for the high-sensitivity measurement) is a small portion (for example, 1/1000) of the measurement window (0 to $M_{max}$) for the low-sensitivity measurement. In view of the above, the offset voltage $V_{offset}$ is adjusted in accordance with the above-described steps of FIG. 13 so as to adaptively move the measurement window for the high-sensitivity measurement, whereby the amount of particulates can be measured accurately, irrespective of the amount of particulates at that point in time.

According to the above-described particulate measurement system of the first embodiment, the measurement window of the high-sensitivity measurement signal $SS_{esc}$ is adaptively moved in accordance with the voltage level of the low-sensitivity measurement signal $SW_{esc}$. Therefore, the amount of particulates can be measured accurately irrespective of whether the amount of particulates is large or small. Also, since adjustment of the measurement window of the high-sensitivity measurement signal $SS_{esc}$ is performed by adjusting the offset voltage $V_{offset}$ supplied to the input terminal of the amplification circuit AMP2, the measurement window can be adjusted using a simple circuit configuration. Further, in the first embodiment, the sensor control section 600 supplies to the offset voltage adjustment circuit 745 the offset signal $S_{offset}$ having a signal level determined on the basis of the voltage level of the low-sensitivity measurement signal $SW_{esc}$ so as to cause the offset voltage adjustment circuit 745 to adjust the offset voltage $V_{offset}$, to thereby adaptively change the measurement window of the high-sensitivity measurement signal $SS_{esc}$. Therefore, adjustment of the measurement window can be performed accurately. Also, the low-sensitivity measurement signal $SW_{esc}$ and the high-sensitivity measurement signal $SS_{esc}$ are produced based on the current corresponding to the difference between the amount ions generated from the ion generation section 110 and the amount of ions trapped in the trapping section 130. Therefore, even when the amount of particulates contained in the gas is very small, accurate measurement is possible.

D. Modifications:

The present invention is not limited to the above-described embodiment, and can be implemented in various forms without departing from the scope of the invention.

First Modification:

The configuration of the particulate measurement system 10 of the first embodiment is an example, and the present invention can be realized by a configuration other than that of the particulate measurement system 10 of the first embodiment. For example, the particulate measurement system 10 need not have the second electrode 132. Also, the particulate measurement system 10 may be configured such that the ion generation section 110 is provided separately from the particulate sensor 100 rather than being provided inside the particulate sensor 100. Further, the first electrode 112 may be disposed in the electrification chamber 121 such that the first electrode 112 penetrates the partition wall 42, whereby corona discharge is produced between a forward end portion of the first electrode 112 and the inner wall surface of the electrification chamber 121. In this case, the ion generation section 110 and the exhaust gas electrification section 120 are united. Also, the measurement signal generation circuit 740 may have any of various configurations other than the configuration described in the embodiment so long as the measurement signal generation circuit 740 can generate a signal representing the amount of particulates.

Second Modification:

The particulate measurement system 10 of the above-described embodiment is configured to generate positive ions between the first electrode 112 and the partition wall 42 by producing corona discharge. However, the particulate measurement system 10 may be configured to generate negative ions by producing corona discharge. For example, negative ions can be generated between the first electrode 112 and the partition wall 42 by switching the polarities of the first electrode 112 and the partition wall 42 such that the first electrode 112 becomes negative and the partition wall 42 becomes positive.

The invention has been described in detail with reference to the above embodiments. However, the invention should not be construed as being limited thereto. It should further be apparent to those skilled in the art that various changes in form and detail of the invention as shown and described above may be made. It is intended that such changes be included within the spirit and scope of the claims appended hereto.

This application is based on Japanese Patent Application No. 2013-222167 filed Oct. 25, 2013, incorporated herein by reference in its entirety.

What is claimed is:

1. A particulate measurement system comprising:
    (a) a particulate sensor including:
        an ion generation section for generating ions by corona discharge;
        an electrification chamber for electrifying at least a portion of particulates contained in exhaust gas discharged from an internal combustion engine of a vehicle with said ions; and
        a trapping section for trapping at least a portion of the ions not used for electrification of the particulates;
    (b) a sensor drive section configured to communicate with the particulate sensor, the sensor drive section including:
        a sensor circuit section including:
            a measurement signal generation circuit for generating a measuring signal correlating with an amount of particulates contained in the exhaust gas, based on a current corresponding to a difference between an amount of ions generated by the ion generation section and an amount of ions trapped in the trapping section; and
        a sensor control section including a microcomputer configured to execute instructions configured to:
            determine the amount of particulates contained in the exhaust gas based on the measurement signal,
            obtain one or a plurality of operating condition parameters of the vehicle selected from the group consisting of a speed of the vehicle, a rotational speed of the internal combustion engine and a torque of the internal combustion engine, and
            correct the measurement signal or the amount of particulates determined from the measurement signal with a correction function based on one or a plurality of the operating condition parameters as input variables of the correction function.

2. The particulate measurement system as claimed in claim 1, wherein the correction is performed based on all of the operating condition parameters.

3. The particulate measurement system as claimed in claim 1, wherein the correction is performed in accordance with the following equation:

$$y = y_0 \times \alpha(Vh) \times \beta(Neg) \times \gamma(Teg)$$

wherein y is the measurement signal or the amount of particulates after correction, $y_0$ is the measurement signal or the amount of particulates before correction, Vh is the speed of the vehicle, Neg is the rotational speed of the internal combustion engine, Teg is the torque of the internal combustion engine, and $\alpha(Vh)$, $\beta(Neg)$ and $\gamma(Teg)$ are coefficients determined in accordance with corresponding parameters Vh, Neg and Teg, respectively.

4. The particulate measurement system as claimed in claim 3, wherein each of the coefficients $\alpha(Vh)$, $\beta(Neg)$ and $\gamma(Teg)$ is a step function which provides a fixed coefficient value for each of a plurality of ranges of corresponding parameters Vh, Neg and Teg.

5. The particulate measurement system as claimed in claim 1, wherein the correction is performed in accordance with the following equation:

$$y = y_0 \times \delta(Vh, Neg, Teg)$$

wherein y is the measurement signal value or the amount of particulates after correction, $y_0$ is the measurement signal value or the amount of particulates before correction, Vh is the speed of the vehicle speed, Neg is the rotational speed of the internal combustion engine, Teg is the torque of the internal combustion engine, and δ(Vh, Neg, Teg) is a coefficient determined in accordance with corresponding parameters Vh, Neg and Teg.

* * * * *